Jan. 15, 1946. W. SIM Plant Pat. 669
CARNATION PLANT
Filed Feb. 1, 1945
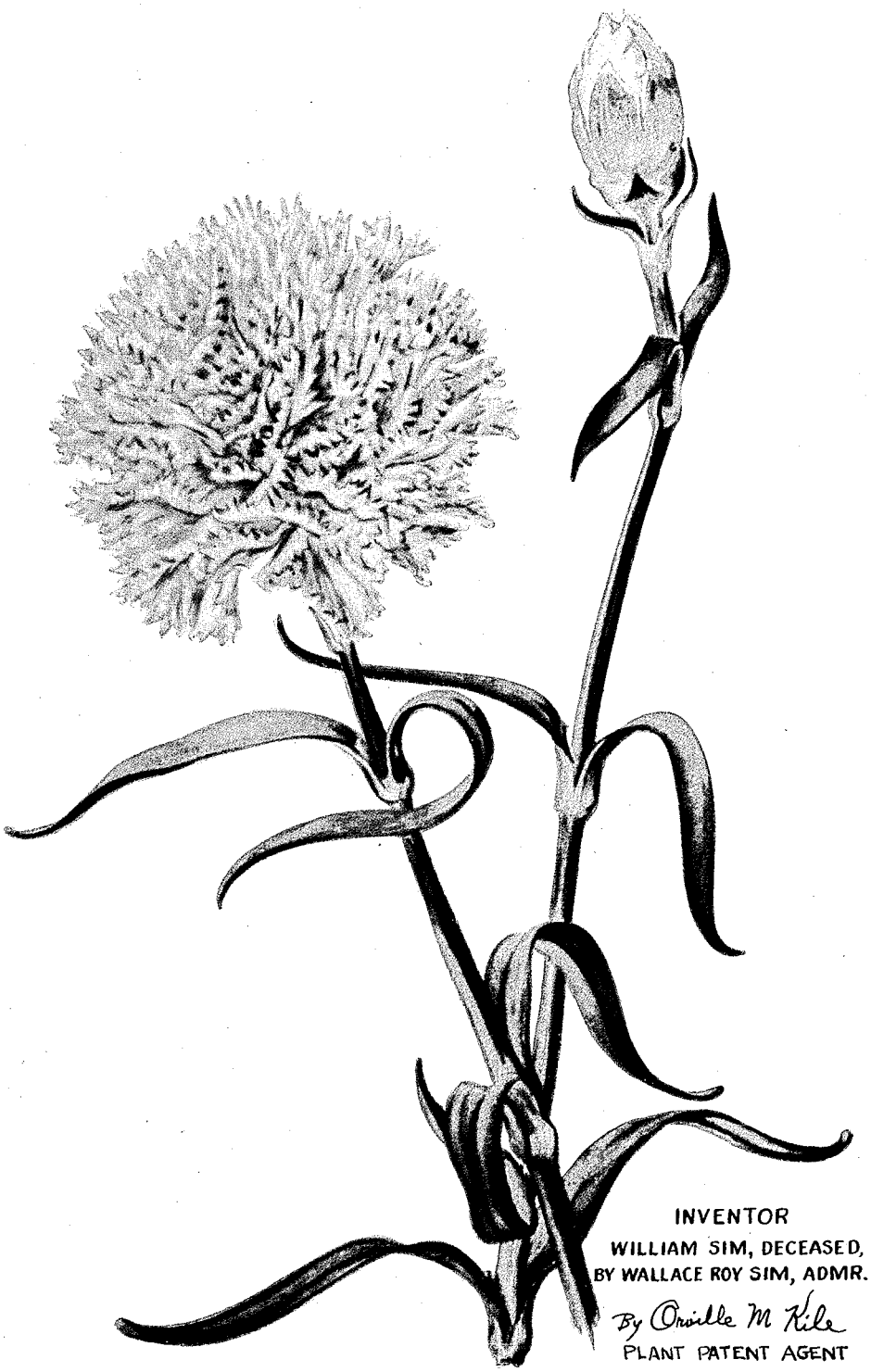
INVENTOR
WILLIAM SIM, DECEASED,
BY WALLACE ROY SIM, ADMR.
By Orville M Kile
PLANT PATENT AGENT Patented Jan. 15, 1946

UNITED STATES PATENT OFFICE

669

CARNATION PLANT

William Sim, deceased, late of North Berwick, Maine, by Wallace Roy Sim, administrator, North Berwick, Maine, assignor to Patten & Company, Tewksbury, Mass.

Application February 1, 1945, Serial No. 575,697

1 Claim. (Cl. 47—60)

The present invention relates to improvements in red carnation varieties of the large-flowered forcing type. The variety originated as a seedling in the greenhouses of Wm. Sim & Son, at North Berwick, Maine. Although of unknown parentage, it is the result of breeding efforts carried on by the inventor for many years, to develop new varieties and strains of carnations.

This new variety has a combination of more of the features accepted by the florist trade as desirable, than has any other variety of carnation known to the inventor. It has uniform growth, a good strong stem, non-splitting calyx, flower of large size and rich, deep color, very high productivity, high standard of quality throughout the season, and can easily be brought into bloom for Christmas when red carnations are particularly desirable.

The accompanying illustration shows a flower and a bud of this new variety which in the original paintings are as true to color as it is possible for the artist to portray them.

Following is a detailed description of the flower and plant of this new variety. Plate references indicate Ridgway's Color Standards and Nomenclature.

*The plant*

Growth: Vigorous and upright, producing a very symmetrical plant without scraggly surplus shoots. Plants from indoor culture attain a height of 3½ feet by January 1st and 4½ feet by March 1st. Uniform high quality is maintained throughout the season. Side shoots grow very rapidly and unless removed when ready for cuttings they will develop into flowering stems within a few days.

Flowering habit: Very productive of good blooms. Plants can be forced for Christmas flowering. Quality and size of flowers is maintained throughout the season.

Stems: Very strong and upright. *Internodes* 3½ to 4 inches long. *Nodes* large.

*Color.*—Approximately Forest Green (Pl. XVII), covered with gray bloom.

Foliage:

*Size.*—Average 4 inches long and ⅜ to ½ inch broad.

*Habit.*—Non-curling.

*Color.*—Same as stems.

*Quantity.*—Average.

*The flower*

Bud:

*Size.*—Large, with diameter about 1¼ inches.

*Form.*—Short and with very large opening.

*Color.*—Between Scarlet Red and Carmine (Plate I). Probably could be called dark-Scarlet-Red, although no such color is shown on the Ridgway plate.

*Opening.*—Slow and perfect.

Flower:

*Size.*—Very large, averaging about 4 inches in diameter under ordinary greenhouse culture.

*Color.*—The same rich dark scarlet-red as the bud. This color does not change during the lifetime of the flower.

*Form.*—Full-petaled, high-centered and regular, with outer edge almost an unbroken circle.

*Petalage.*—From 45 to 55 petals in the winter months, with 52 to 55 petals about December 1st.

*Calyx.*—Approximately Biscay Green (Plate XVII), with bracts of much darker green. 1¼ to 1⅜ inches long and ¾ inch wide (1 inch wide if flattened). Very strong, tough and non-splitting—this latter feature being a great advantage in so large a flower.

*Longevity.*—Flowers last longer when cut than any red variety known to me.

*Fragrance.*—Mild and pleasant.

*Petals.*—Slightly fringed but not deeply cut. Guard petals are 1 to 1½ inches in width and spread to form almost a perfect circular plane. Other petals are folded and tightly bunched together so that separate petals are not distinguishable.

Reproductive organs:

*Ovary.*—Large; high; pithy.

*Pistils.*—Small; pinkish tinged; curved but not curled; from ¾ to 1¼ inches long; usually divided into 2 or 3 branches; seldom long enough to be visible in the open flower.

*Stamens.*—White; few; ragged and without anthers.

*Comparisons*

The two varieties which are most like this new variety are the subjects of Plant Patents No. 148 and No. 463, but they differ principally in the following points.

Comparison with No. 148:

1. This new variety has larger blooms than those of No. 148.
2. This variety has no excessive growth such as is found in No. 148.
3. This variety has better shipping and keeping qualities.
4. This variety has larger buds with larger openings.
5. This variety has heavier and stiffer stems.
6. This variety has larger blossoms with greater petalage.
7. Color of flowers of this variety is slightly darker, and its brilliance is retained much better.
8. This variety is more productive of large flowers and a higher quality is maintained throughout the season.

Comparison with No. 463:

1. This new variety has larger blooms than those of No. 463.
2. Blooms of this variety are more regular and less ragged in appearance.
3. Petals of flowers of this variety are less deeply notched.
4. Flowers of this variety have a better keeping quality.
5. This variety has a more uniform growth and maintains a more uniform quality of flowers throughout the season.
6. This variety produces a less scraggly and more symmetrical plant.
7. Growth of cuttings is more rapid in this variety.
8. Productivity of good flowers throughout the season is much greater in this new variety.
9. Foliage of this variety does not curl as does that of No. 463.
10. Buds of this variety have a larger opening and open more evenly and slowly.

Having thus disclosed this discovery, I claim for the inventor:

The new and distinct variety of carnation plant substantially as herein shown and described, characterized by its combination of features including particularly its symmetrical and rapid growth; its great productivity; its long heavy stems; its bud with large opening and tough calyx; its very large dark scarlet-red flowers of uniformly good quality throughout the season; and the exceptionally good shipping and keeping qualities of its flowers.

WALLACE ROY SIM,
*Administrator of the Estate of William Sim, Deceased.*